United States Patent [19]

Wagle et al.

[11] 4,248,800

[45] Feb. 3, 1981

[54] MANUFACTURE OF ORGANIC HYDRAZINES

[75] Inventors: Uday D. Wagle, Morgan Hill, Calif.; Timothy J. Belford, Tonawanda, N.Y.

[73] Assignee: Pennwalt Corporation, Philadelphia, Pa.

[21] Appl. No.: 22,742

[22] Filed: Mar. 22, 1979

[51] Int. Cl.$^2$ .................. C07C 109/02; C07C 109/04
[52] U.S. Cl. .................................................. 564/464
[58] Field of Search ................ 260/583 B, 569, 563 R

[56] References Cited

U.S. PATENT DOCUMENTS

| | | | |
|---|---|---|---|
| 2,710,248 | 6/1955 | Sisler et al. | 260/583 B X |
| 2,806,851 | 9/1957 | Sisler et al. | 260/589 X |
| 2,808,439 | 10/1957 | Barrett et al. | 260/583 B |
| 2,901,511 | 8/1959 | Hurley | 260/583 B |
| 4,013,758 | 3/1977 | Osborg | 260/583 B X |
| 4,066,698 | 1/1978 | Clasen | 260/569 |

FOREIGN PATENT DOCUMENTS

| | | | |
|---|---|---|---|
| 2528733 | 1/1977 | Fed. Rep. of Germany | 260/569 |
| 1274393 | 9/1961 | France | 260/583 B |
| 1343451 | 10/1963 | France | 260/583 B |

*Primary Examiner*—John Doll

[57] ABSTRACT

A chloramine generator is used in the manufacture of organic hydrazines wherein water is introduced into the generator to prevent plugging by the by-product ammonium chloride while preventing the chloramine from dissolving in the water. The chloramine is discharged directly into the hydrazine reactor without isolation of chloramine as an intermediate.

4 Claims, 2 Drawing Figures

MANUFACTURE OF ORGANIC HYDRAZINES

BACKGROUND OF THE INVENTION

This invention relates to a process and an apparatus for the one-step manufacture of organic hydrazines in aqueous solutions.

Substituted hydrazines play an important role as intermediates in pharmaceuticals, rocket fuels and starting materials for azo compounds. Prior to the instant invention, there were several methods of preparing hydrazines: one of the commercially significant methods involves starting from chloramine or substituted chloramine and reacting the chloramine with an amine to obtain the desired product. Since chloramine is highly reactive and unstable, in order for a commercial process to be successful, a large quantity of chlorine must be used.

Audrieth, et al. (JACS, 76, 4869, 1954) describes a process for making substituted hydrazine by utilizing aqueous chloramine as a raw material. The preparation of chloramine in an aqueous solution is difficult and must be carried out at low temperatures (about $-15°$ C.) and the amount of alkali in the system must be controlled. Further, only dilute solutions are stable. Sissler, et al. (JACS, 73, 1619, 1951; JACS, 76, 3906, 1954) uses gaseous reactants to prepare substituted hydrazines. This involves the reaction of anhydrous gaseous ammonia with anhydrous chlorine; nitrogen is used as a carrier gas. This method suffers from the by-product of reaction, ammonium chloride, depositing on the reactor walls and plugging up the reactor in a matter of minutes (i.e., 10 to 15 minutes). A later work of Sissler, et al. (ALLEG. PRAKT. CHEM. 21, No. 4, 123–124) describes one way to overcome this problem: the reaction zone is maintained above the sublimation temperature of ammonium chloride. However, this allows only a little more time before the reactor is plugged up. A recent German patent application (Offenlegungschrift No. 24 40 225) describes the addition of a coolant through a split ring to cause ammonium chloride to condense as a fine powder which is carried away from the reaction zone. A large volume of the nitrogen coolant must be used which leads to the dilution of the chloramine; subsequent recovery of excess reactants is made proportionately more difficult. Since some deposition of ammonium chloride takes place, a vibrator is used to loosen the deposits from time to time. The reaction zone is also maintained at a higher temperature to prevent deposits from occurring.

The process of the present invention overcomes the disadvantages of the prior art because the present invention is a one-step process for the manufacture of substituted hydrazines that is carried out at convenient temperatures.

STATEMENT OF THE INVENTION

The present invention is directed to a process for the manufacture of substituted hydrazines comprising:

a. reacting in a first reaction zone having a length to diameter ratio of 6 to 20 and is resident within a second reaction zone, gaseous chlorine admixed with nitrogen gas and gaseous ammonia to produce gaseous chloramine and ammonium chloride in a temperature range of 25° to 350° C.;

b. introducing water into the first reaction zone through an inlet after the chloramine has been produced to prevent plugging of the reactor by the ammonium chloride while preventing the chloramine from dissolving in the water;

c. introducing the nitrogen carrier gas into the first reaction zone at a velocity sufficient to dilute the chloramine stream and reduce the driving force for transfer of chloramine from the gaseous phase into the water;

d. reacting in the second reaction zone, in the gaseous chloramine produced in the first reaction zone directly with an aqueous alkali metal hydroxide and a substituted amine having the structure $R_1R_2NH$ wherein:

$R_1$ is hydrogen or linear alkyl of 1 to 8 carbons; and
$R_2$ is selected from the group consisting of linear alkyl of 1 to 8 carbons, secondary alkyl of 3 to 10 carbons, tertiary alkyl of 4 to 12 carbons, aralkyl of 7 to 13 carbons, substituted or unsubstituted cycloalkyl of 3 to 12 carbons and substituted or unsubstituted aryl of 6 to 12 carbons, the substituent being a linear or branched alkyl of 1 to 8 carbons, the second reaction zone being vigorously agitated to insure a complete reaction and being maintained in a temperature range of $-5°$ to $50°$ C.; and e. recovering the substituted hydrazine product in the aqueous phase from the second reaction zone.

DETAILED DESCRIPTION OF THE INVENTION

It has been discovered that substituted hydrazines can be produced safely in a batch or continuous manner in a single reactor in high yield with the improvement of introducing water into a moderate temperature chloramine generator for dissolving the ammonium chloride formed in the generator without substantially mixing the water with the chloramine. Although it is well known in the art that ammonium chloride is highly soluble in water, it has not been used in the manufacture of chloramine for keeping the reactor clean because it is also known in the prior art that water readily absorbs chloramine; an aqueous solution of chloramine, even in dilute solutions, is unstable at temperatures as low as 0° C. Thus, if water is introduced into the system, a high temperature in the reaction zone and a high heat of mixing for chloramine and water system occur making recovery of chloramine impossible. This fact is demonstrated in Example 5.

The chloramine produced in the generator in a temperature range of 25° to 350° C. (preferably 25° to 200° C.) is carried through the generator by a carrier gas such as nitrogen and is directly introduced into an aqueous stream of a substituted amine, $R_1R_2NH$ (where $R_1$ and $R_2$ are defined as above), an alkali metal hydroxide and gelatin. This reaction is carried out at $-5°$ to $50°$ C., preferably 0° to 10° C.

The gaseous chloramine is generated continuously and added to either a batch reaction mass composed of a substituted amine, an alkali metal hydroxide and a metal sequestering agent; or the amine, aqueous alkali metal hydroxide and metal sequestering agent are metered continuously into the reaction zone. If the mode of operation is batchwise, no product is taken out of the reactor until the required amount of chloramine has been generated and added to the reaction mass. For continuous operation, the reactor is filled up to a predetermined level and maintained there by continuously withdrawing product from it.

Batch Procedure

Figure 1:
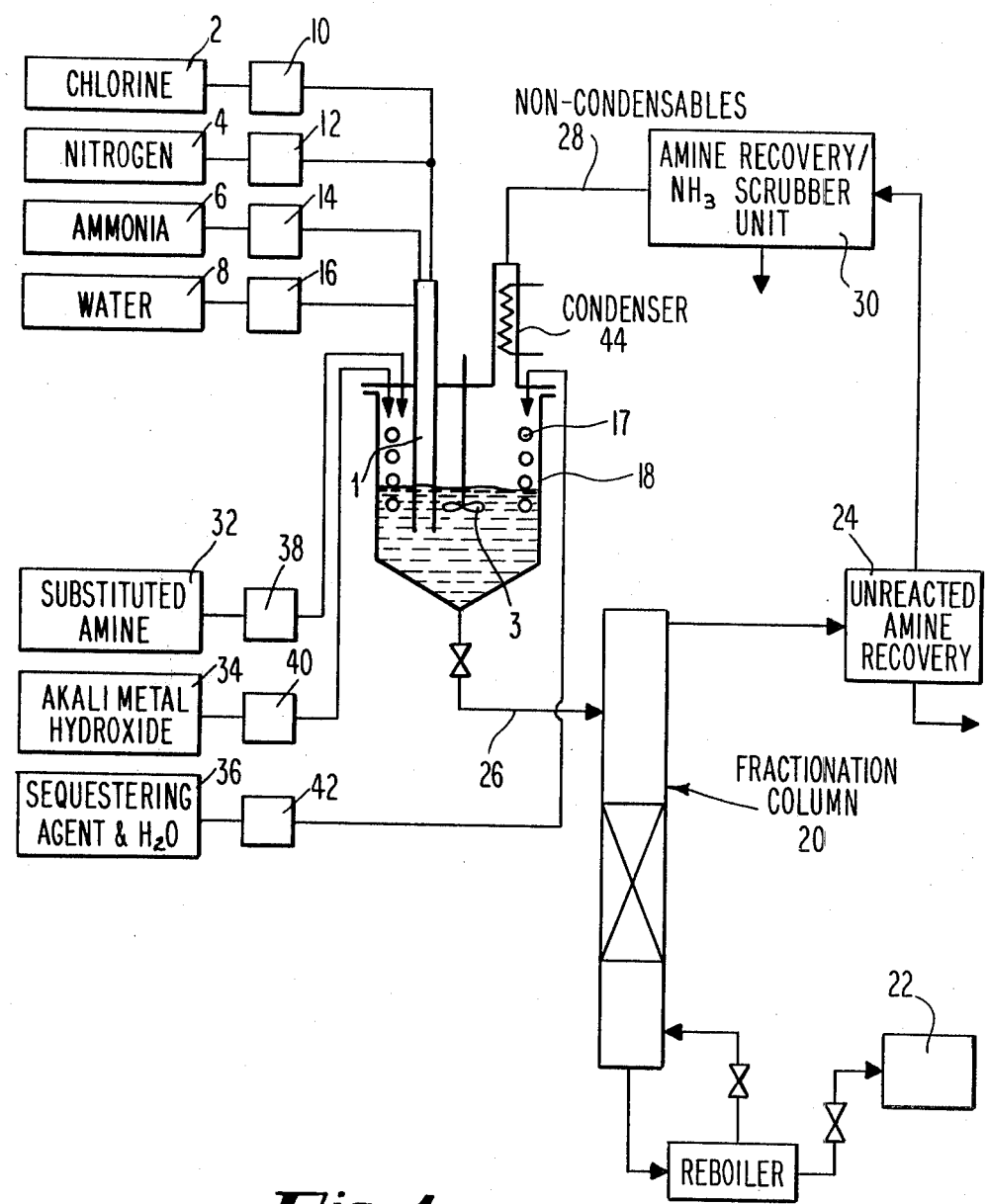
FIG. 1 is a schematic illustration of the process.

Referring to FIG. 1, the reactor (18) is charged with a known amount of substituted amine from storage (32) through metering device (38), an alkali metal hydroxide from storage (34) through a metering device (40) and water to which sequestering agent has been added from storage (36) through metering device (42). The sequestering agent may alternatively be added to the metal hydroxide solution. Then chlorine, nitrogen, ammonia and water from storage tanks (2, 4, 6, 8) are metered through suitable measuring devices (10, 12, 14, 16) into the chloramine generator (1) which discharges into the reactor (18). The chlorine, nitrogen, ammonia and water are continued to be introduced into the generator (1) until the required amount of chloramine has been produced and introduced to reactor (18). The cooling and agitation are started once the reactants are added to reactor (18) and are continued until the reaction is over and the reactor (18) is drained. The reflux condenser (44) on the reactor is cooled with brine solution at $-10°$ to $-18°$ C. to condense as much of volatile components as possible. The non-condensables (28) are sent to an amine recovery unit and scrubber (30) to remove excess ammonia before venting.

Continuous Procedure

For a continuous run, known amounts of amine, alkali hydroxide and sequestering agent are added from storage (32, 34 and 36) through suitable metering devices to reactor (18). Ammonia, nitrogen, chlorine and water are then introduced to generator (1). When the required amount of chloramine has been generated, the amine, aqueous alkali metal hydroxide and sequestering agent are started again to be metered into (18). At the same time, the reactor contents are withdrawn as a stream (26). The gaseous effluent is treated in the same manner as given above for batch runs.

The stream (26) containing the product hydrazine and unreacted raw materials is fractionated to recover the unreacted amine (24) and yield an aqueous solution of the product (22).

The fractionating column (20) is a packed column with a condenser, a reflux splitter, a reboiler and a feed inlet. The reboiler is maintained at a temperature of 70°–170° C. (preferably 90°–100° C.) sufficient to drive off the amine. The overhead condenser is cooled with brine or ice water in a temperature range of 0° C. to $-18°$ C. The overhead gases are sent to the amine recovery unit and ammonia scrubber (30). The separation may be carried out not only by a packed column but by a variety of devices described in literature and available commercially. This includes batch/continuous fractionating units, tray columns, packed columns, etc.

Figure 2:
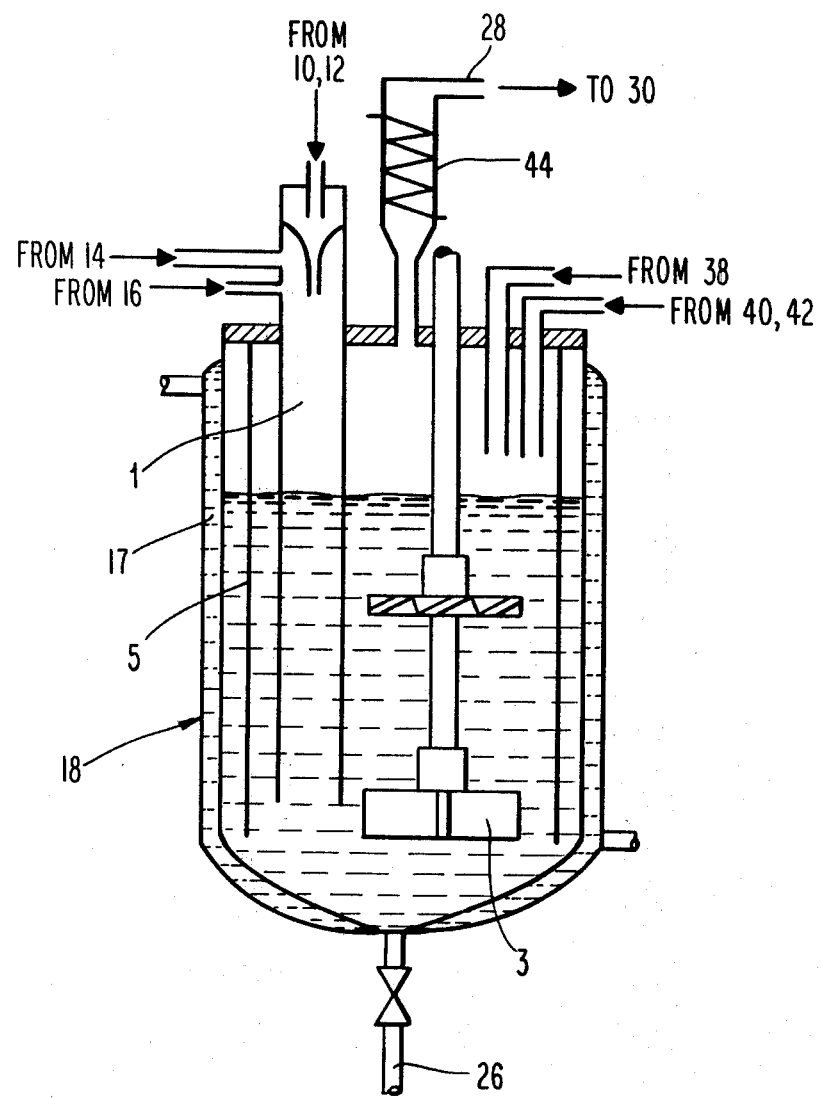
FIG. 2 is a diagrammatic cross-sectional view depicting the intimate relationship of the chloramine and hydrazine reactors.

Details of the reactor are shown in FIG. 2. It shows a reactor (18) fitted with a cooling jacket (17) (cooling coils may also be used), reflux condenser (44), internal baffles (5), an agitator (3), inlet for introducing the aqueous solution of the alkali metal hydroxide, an inlet for adding the substituted amine and the chloramine generation zone (1). The chloramine generator (1) has a chlorine inlet and an ammonia inlet. Nitrogen is added through the same inlet as chlorine. The arrangement shows water being added through an inlet after the ammonia inlet. The chloramine generator is chosen to have a length to diameter ratio in the range of 6 to 20, preferably 7–15. Shorter generators lead to incomplete reaction. Longer generators tend to reduce the chloramine yield because more of the chloramine is dissolved in water. The generator (1) is resident within and opens directly into reactor (18). This arrangement provides the one-step reaction since the chloramine forms rapidly prior to reacting with the amine to form the hydrazine.

The nitrogen flow rate in this arrangement should be at least 10% of the total gases (nitrogen, ammonia and chlorine). Lower percentages reduce overall yield, perhaps due to chloramine dissolving into water.

Another requirement for satisfactory operation of the generator is that the chloramine generator be free of any packing down stream from the reaction zone. A packing would increase mixing of the gaseous stream and the aqueous ammonium chloride solution and this would lead to low overall yields due to distribution of chloramine.

The gases (nitrogen, chlorine and ammonia) are anhydrous technical grade (99+% pure). The amine is at least 90% pure, preferably at least 95%. Agents used for complexing include gelatin and sequestering agents such as EDTA, which is known in the prior art.

The molar ratio of other reactants to chlorine are: amine 1:1 to 20:1, preferably 3:1 to 15:1, ammonia 2:1 to 10:1, preferably 4:1 to 8:1, alkali metal hydroxide, 2:1 to 5:1, preferably 2.5:1 to 3.5:1. The flow rate of water is 1.5 gms/cm-min of generator circumference, which is within range 0.5 to 3 gm/cm-min.

The following examples illustrate the present invention but are not intended to limit the invention thereto.

EXAMPLE 1

To the reactor (18) were charged 310 grams of t-butyl amine, 190 grams of potassium hydroxide (25%) and 2 grams of gelatin. Nitrogen flow was started at 1000 cc/minute, the ammonia flow at 2.45 grams/min and chlorine flow at 1.5 grams per minute. After 20 grams of chlorine were added, t-butyl amine at 23 grams/minute and 25% potassium hydroxide (to which gelatin to the extent of 1% had been added) at 14.1 grams/minute were started. Water flow was started and maintained throughout the run at 5 grams/minute. The reactor was maintained at 6° C. The product was withdrawn to maintain a constant level in the reactor. The run was stopped after a total of 180 grams of chlorine and 294 grams of ammonia had been reacted. The crude t-butyl hydrazine assaying at 2.2% was stripped to obtain 4285 grams of aqueous t-butyl hydrazine. The t-butyl amine recovery unit yielded 114 grams and the distillate contained 2320 grams of t-butyl amine. t-Butyl amine was recovered and recycled. The yield based on chlorine was 69%. The t-butyl hydrazine was assayed by iodate method. A sample was checked for hydrazine and no hydrazine was found. The run lasted 120 minutes without plugging and could have been continued if desired.

EXAMPLE 2

To the reactor (18), were charged 294 grams of t-butyl amine, 331 grams of 25% potassium hydroxide and 2 grams of gelatin. Nitrogen, ammonia and chlorine were added to generator (1) at a flow rate of 1000 cc/min, 2.4 grams/min and 1.5 grams/min, respectively. The reaction was continued at the above mentioned flow rates until 35 grams of chlorine had been added. At that time the three flow rates for nitrogen, ammonia and chlorine were stopped. The reaction temperature was maintained at 6° C. Water was added through the generator (1) at 5 grams/minute. The run gave 68.6% yield based on chlorine, 3.15% assay t-butyl hydrazine.

EXAMPLE 3

The same procedure as Example 2 was followed using 144 grams of t-butyl amine, 425 grams of potassium hydroxide (25%), and 2 grams of gelatin, 40 grams of chlorine, 67 grams of ammonia, and about 145 grams of water were added to the generator. The yield was 56% of t-butyl amine, assaying at 2.50%.

EXAMPLE 4

In this example, no water was used. To the reactor (18), 400 grams of t-butyl amine, 464 grams of 10% sodium hydroxide and 150 ml of 1% gelatin in water were charged. Nitrogen, ammonia and chlorine were added to the generator and maintained at a flow rate of 1000 cc/min, 2.35 grams/min, 1.25 grams/min, respectively. The flow rates were continued for 20 minutes and then stopped. The reaction temperature was 20°–30° C. The yield was 68.6% based on chlorine. Since no water was added through the generator, a large deposit of ammonium chloride accumulated in the generator blocking it completely. This example demonstrates that by omitting the water the reactor would have to be cleaned before reusing or for continued use.

EXAMPLE 5

In this example, the water was well mixed with the gaseous chloramine just before the chloramine stream entered the aqueous reaction mass. For this, the apparatus was modified to include an orifice at the end of the generator and the generator was external to the reactor and the gaseous stream entered through an opening in the side of the reactor.

200 grams of t-Butyl amine, 232 grams of 25% sodium hydroxide and 2 grams of gelatin were added to the reactor. Nitrogen, ammonia and chlorine were added to the generator and maintained at 1000 cc/min, 1.44 g/min, and 1.5 g/min respectively. Water was introduced at 5.6 g/min. The flow rate of t-butyl amine was 13 g/min; sodium hydroxide was 10.6 grams/min; 1% gelatin in water was 5 grams/min. The run was continuous for 30 minutes. No t-butyl hydrazine was found in the reactor effluent. This example demonstrates that if water is introduced into the system so that it absorbs the chloramine, the high temperature in the reaction zone and high heat of mixing for the chloramine-water system makes recovery of chloramine impossible.

EXAMPLE 6

In Example 5, water was omitted and the yield went up to 30% based on chlorine.

What is claimed:

1. A process for the manufacture of substituted hydrazines comprising:
   (a) reacting in a first reaction zone, having a length to diameter ratio of 6 to 20 that is resident within a second reaction zone, gaseous chlorine admixed with nitrogen gas and gaseous $NH_3$ to produce gaseous chloramine and $NH_4Cl$ in a temperature range of 25° to 350° C.;
   (b) introducing water into the first reaction zone through an inlet after the chloramine has been produced to prevent plugging of the reactor by the $NH_4Cl$ but preventing the chloramine from dissolving in the water;
   (c) introducing the nitrogen carrier gas into the first reaction zone at a velocity sufficient to dilute the chloramine stream and reduce the driving force for transfer of chloramine from the gaseous phase into the water;
   (d) reacting in a second reaction zone the gaseous chloramine produced in the first reaction zone directly with an aqueous alkali metal hydroxide and a substituted amine having the structure $R_1R_2NH$ wherein:
   $R_1$ is hydrogen or linear alkyl of 1 to 8 carbons; and
   $R_2$ is selected from the group consisting of linear alkyl of 1 to 8 carbons, secondary alkyl of 3 to 10 carbons, tertiary alkyl of 4 to 12 carbons, aralkyl of 7 to 13 carbons, substituted or unsubstituted cycloalkyl of 3 to 12 carbons and substituted or unsubstituted aryl of 6 to 12 carbons, the substituent being a linear or branched alkyl of 1 to 8 carbons, the second reaction zone being vigorously agitated to insure a complete reaction and being maintained in a temperature range of −5° to 50° C.; and
   (e) recovering the substituted hydrazine product in the aqueous phase from the second reaction zone.

2. The process of claim 1 wherein the flow rate of the water into the first reaction zone is 0.5 to 3 gms./cm-min. of reaction zone circumference.

3. The process of claim 1 wherein the substituted amine is t-butyl amine.

4. The process of claim 1 wherein gelatin is added to the second reaction zone.

* * * * *